United States Patent [19]

Vanderbrook

[11] Patent Number: 5,263,943
[45] Date of Patent: Nov. 23, 1993

[54] VALVED INTRAVENOUS NEEDLE ASSEMBLY

[76] Inventor: Bernard E. Vanderbrook, 206 Oak Grove Park Rd., Dallas, N.C. 28034

[21] Appl. No.: 933,765

[22] Filed: Aug. 24, 1992

[51] Int. Cl.$^5$ ............................................... A61N 5/00
[52] U.S. Cl. ...................................... 604/247; 604/179
[58] Field of Search ............... 604/179, 246, 247, 272, 604/256; 128/DIG. 6, DIG. 15, DIG. 26

[56] References Cited

U.S. PATENT DOCUMENTS

| | | | |
|---|---|---|---|
| 3,834,380 | 9/1974 | Boyd | 128/DIG. 26 |
| 4,468,224 | 8/1984 | Enzmann et al. | 604/247 |
| 4,569,348 | 2/1986 | Hasslinger | 128/179 |
| 4,950,254 | 8/1990 | Andersen et al. | 604/247 |

FOREIGN PATENT DOCUMENTS 0442599  4/1927  Fed. Rep. of Germany ...... 604/247

Primary Examiner—John D. Yasko
Assistant Examiner—Anthony Gutowski
Attorney, Agent, or Firm—Leon Gilden

[57] ABSTRACT

A needle assembly includes an elongate first cylindrical cavity having a first end and a second end, with the second end formed with a conical recess, the conical recess including a through-extending bore in communication with the recess directed into a second cavity, wherein reverse flow of fluid relative to the first cylindrical body is prevented from flow into the second cylindrical body and contamination of intravenous fluid directed into the assembly.

3 Claims, 4 Drawing Sheets

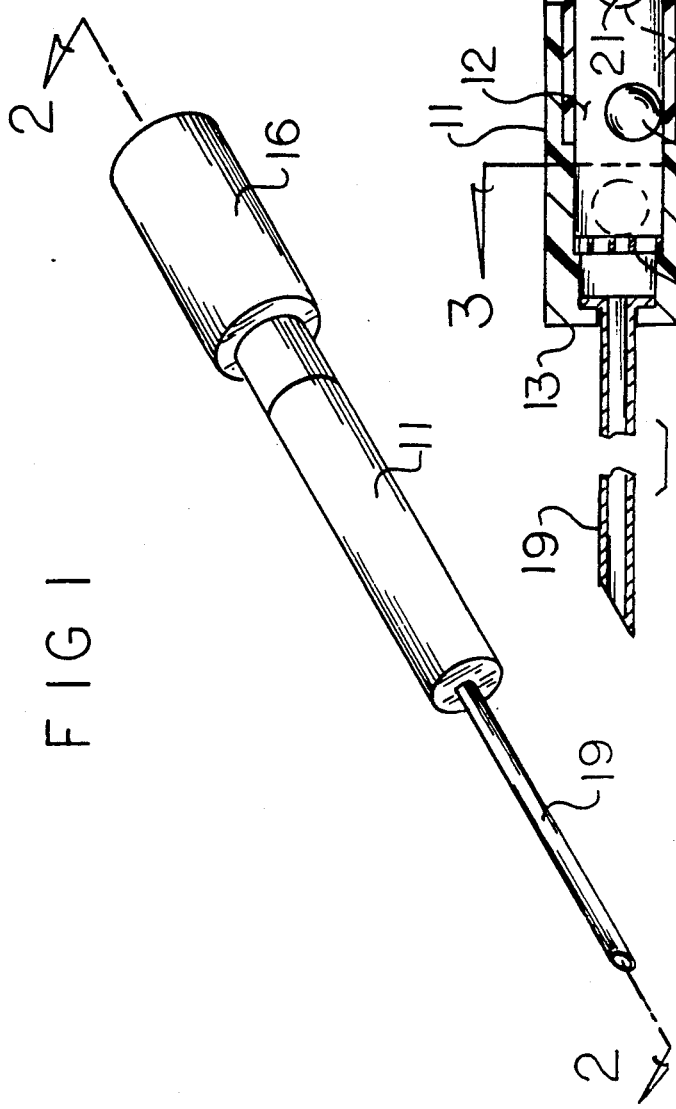

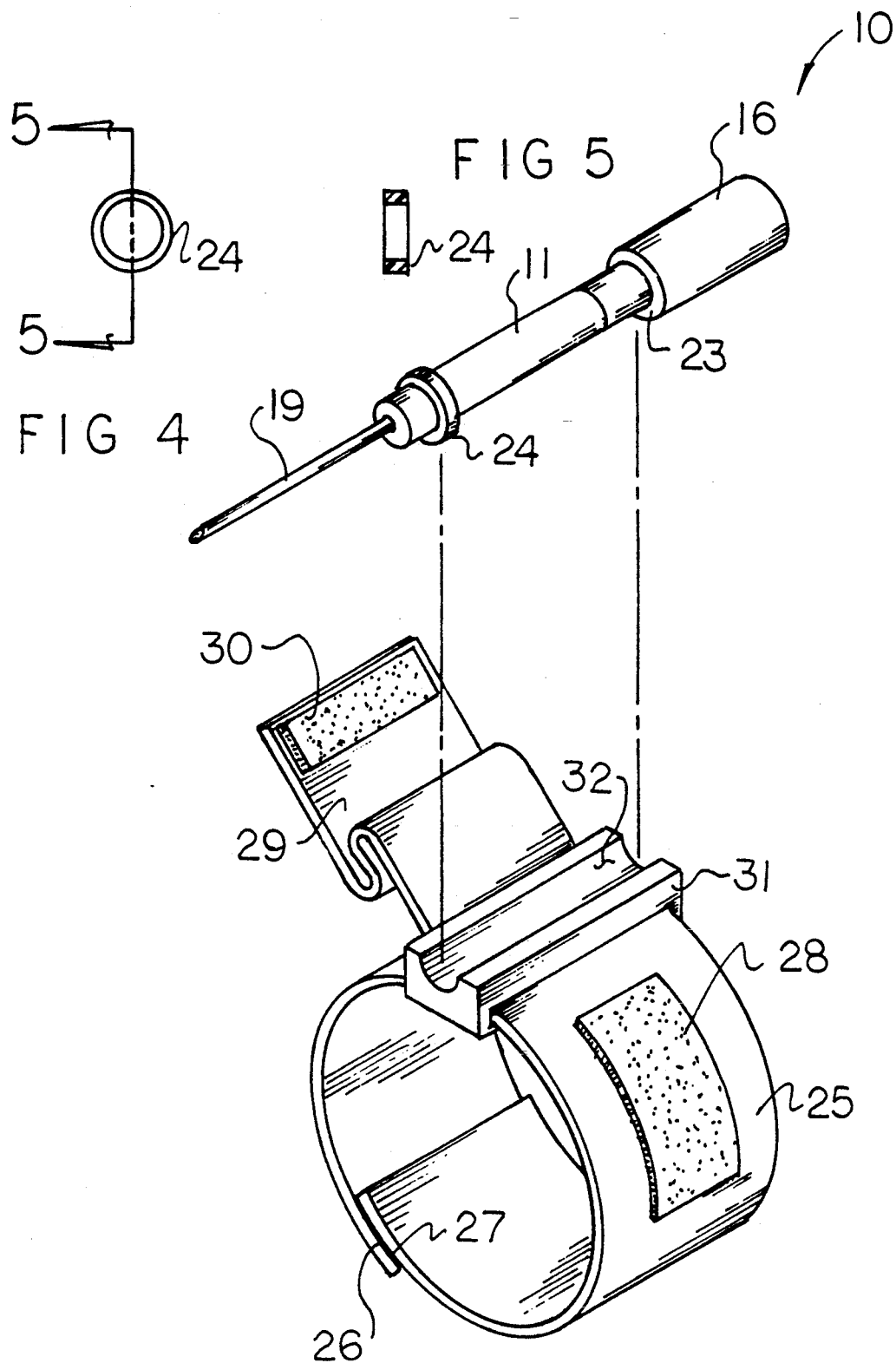

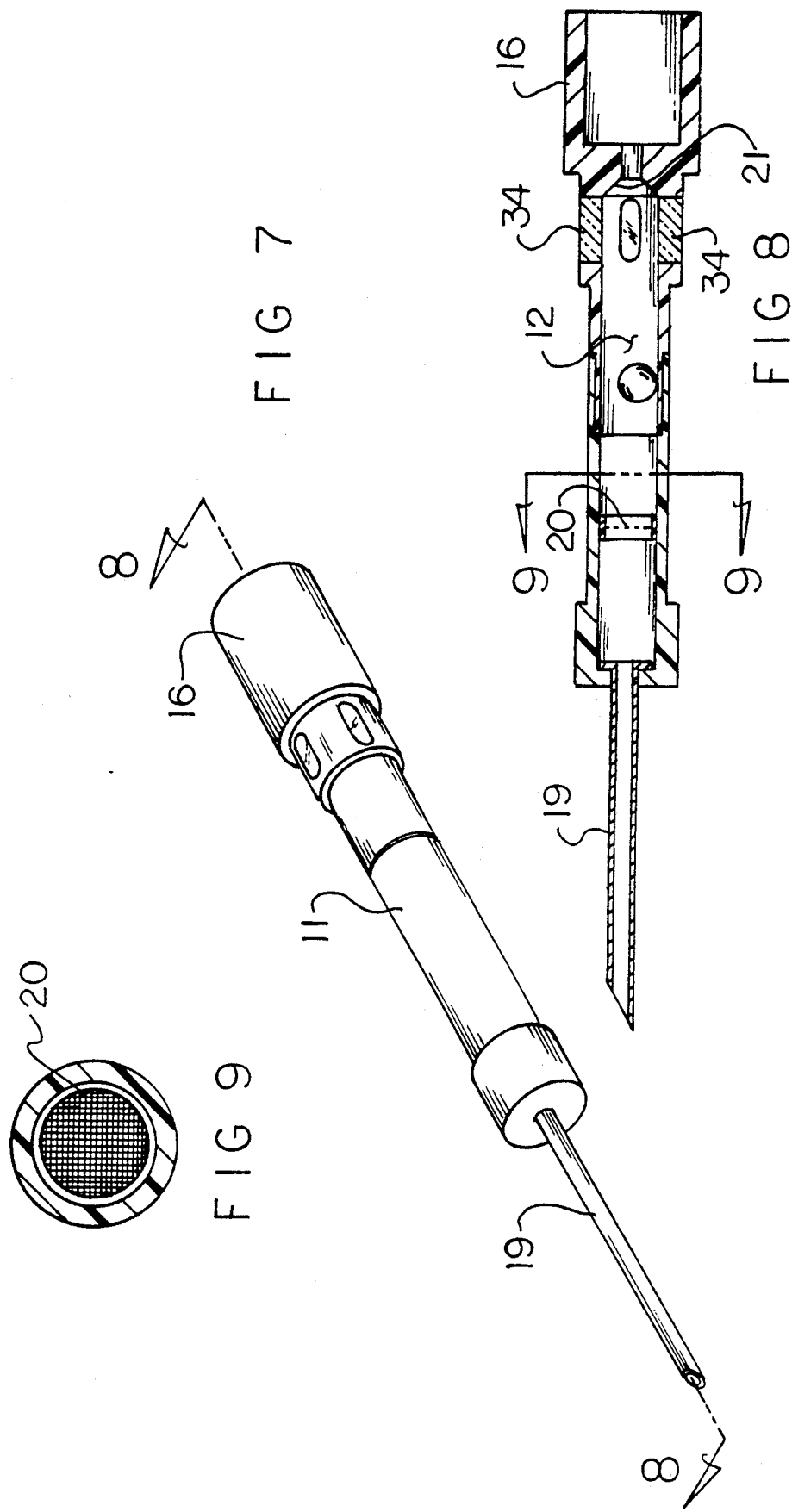

VALVED INTRAVENOUS NEEDLE ASSEMBLY

BACKGROUND OF THE INVENTION

1. Field of the Invention

The field of invention relates to intravenous needle structure, and more particularly pertains to a new and improved valved intravenous needle assembly wherein the same permits reverse flow of intravenous fluid relative to the assembly structure.

2. Description of the Prior Art

The prior art has utilized various valve lines in association with intravenous fluid flow such as exemplified in U.S. Pat. Nos. 4,804,360 and 4,802,650.

The instant invention attempts to provide for a compact housing structure arranged for mounting relative to an individual in association with a needle tube to prevent reverse flow through an associated intravenous feed tube and in this respect, the present invention substantially fulfills this need.

SUMMARY OF THE INVENTION

In view of the foregoing disadvantages inherent in the known types of intravenous flow assembly structure now present in the prior art, the present invention provides a valved intravenous needle assembly wherein the same utilizes a check ball mounted within an elongate body of a unitary intravenous assembly structure. As such, the general purpose of the present invention, which will be described subsequently in greater detail, is to provide a new and improved valved intravenous needle assembly which has all the advantages of the prior art intravenous coupling structure and none of the disadvantages.

To attain this, the present invention provides a needle assembly including an elongate first cylindrical cavity having a first end and a second end, with the second end formed with a conical recess, the conical recess including a through-extending bore in communication with the recess directed into a second cavity, wherein reverse flow of fluid relative to the first cylindrical body is prevented from flow into the second cylindrical body and contamination of intravenous fluid directed into the assembly.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved valved intravenous needle assembly which has all the advantages of the prior art intravenous coupling structure and none of the disadvantages.

It is another object of the present invention to provide a new and improved valved intravenous needle assembly which may be easily and efficiently manufactured and marketed.

It is a further object of the present invention to provide a new and improved valved intravenous needle assembly which is of a durable and reliable construction.

An even further object of the present invention is to provide a new and improved valved intravenous needle assembly which is susceptible of a low cost of manufacture with regard to both materials and labor, and which accordingly is then susceptible of low prices of sale to the consuming public, thereby making such valved intravenous needle assemblies economically available to the buying public.

Still yet another object of the present invention is to provide a new and improved valved intravenous needle assembly which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of the instant invention.

FIG. 2 is an orthographic view, taken along the lines 2—2 of FIG. 1 in the direction indicated by the arrows.

FIG. 3 is an orthographic view, taken along the lines 3—3 of FIG. 2 in the direction indicated by the arrows.

FIG. 4 is an orthographic top view of the abutment ring utilized by the invention.

FIG. 5 is an orthographic view, taken along the lines 5—5 of FIG. 4 in the direction indicated by the arrows.

FIG. 6 is an isometric illustration of a support strap structure for use by the instant invention.

FIG. 7 is an isometric illustration of a modified tube structure utilized by the invention.

FIG. 8 is an orthographic view, taken along the lines 8—8 of FIG. 7 in the direction indicated by the arrows.

FIG. 9 is an orthographic view, taken along the lines 9—9 of FIG. 8 in the direction indicated by the arrows.

DESCRIPTION OF THE PREFERRED EMBODIMENT

Figure 10:
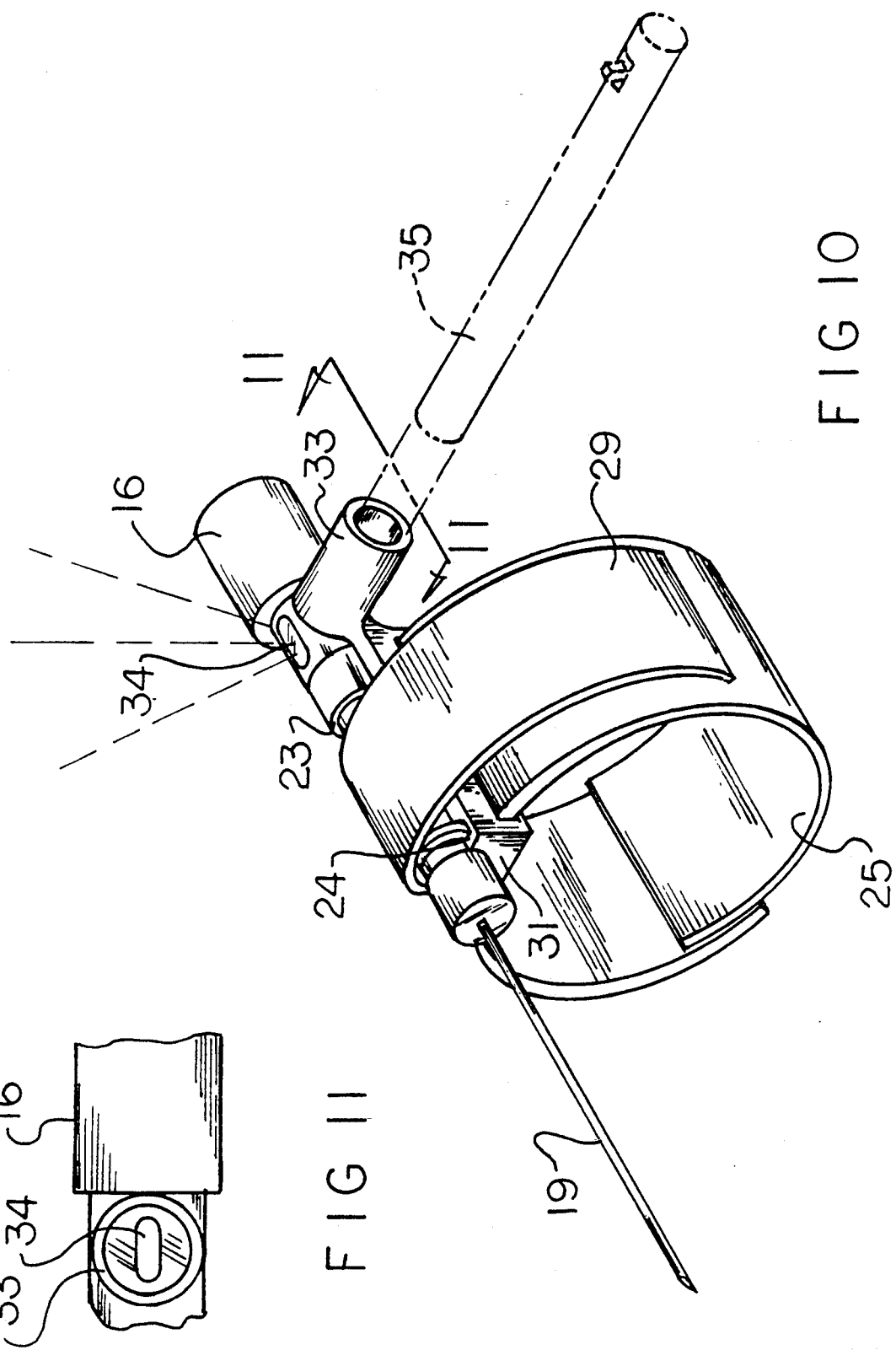
FIG. 10 is an isometric illustration of a modified aspect of the invention.
Figure 11:
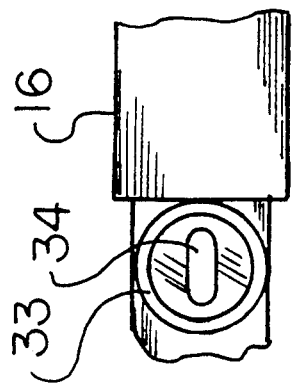
FIG. 11 is an orthographic view taken along the lines 11—11 of FIG. 10 in the direction indicated by the arrows.

With reference now to the drawings, and in particular to FIGS. 1 to 11 thereof, a new and improved valved intravenous needle assembly embodying the principles and concepts of the present invention and generally designated by the reference numeral 10 will be described.

More specifically, the valved intravenous needle assembly 10 of the instant invention includes a first elongate body 11 having a first cylindrical cavity 12 of a predetermined first diameter. The first body 11 includes a first body end wall 13 spaced from a second elongate body 16 at an opposed distal end of the first body 11. The second elongate body includes a second cavity 17 of a second diameter greater than the first diameter to receive an intravenous delivery tube 18 therewithin. A first body web 14 is mounted at an interface of the first cylindrical cavity 12 to the second cavity 17. The web 14 includes a web bore 15 arranged in fluid communication between the first and second cavities 12 and 17.

A needle tube 19 is mounted through the first body end wall 13 in fluid communication with the first cavity 12, with an apertured barrier plate 20 having a matrix of apertures therethrough mounted within the first cavity 12 in adjacency to the first body end wall 13. A conical recess 21 is formed at a second end of the first cavity 12 spaced from the barrier plate 20 and a first body end wall 13. The conical recess 21 is coaxially aligned relative to a first body axis (not shown) about which the first cavity 12 is defined. A spherical plug 22 is floatingly mounted within intravenous fluid that is directed through the first cavity 12 from the second cavity 17. In normal fluid flow from the second cavity to the first cavity, the spherical plug having a plug diameter less than the first diameter is imposed upon the barrier plate, as illustrated in phantom in FIG. 2, with fluid flow directed about the spherical plug 22 through the barrier plate and through the needle tube 19. Upon reverse flow from the needle tube into the first cavity 12, the spherical plug 22 is directed into the conical recess 21 to effect blockage of the web bore 15 preventing reverse flow into the second cavity from the first cavity and contamination of intravenous fluid within the delivery tube 18.

The FIG. 6 indicates the use of an abutment ring 24 mounted about the first body 12 in a spaced relationship relative to a first body first end wall 23. The first body first end wall 23 is spaced from the abutment ring 24 a predetermined length. A cradle support 30 is provided having a semi-cylindrical cavity 32, wherein the semi-cylindrical cavity is of a length equal to the predetermined length to thereby securely position the first body relative to the cradle 31. The cradle support 31 is mounted to a mounting strap 25 for securement about an individual's limb in positioning of the intravenous needle tube 19. The mounting strap 25 includes respective mounting strap first and second fasteners 26 and 27 at opposed free ends of the mounting strap for securement of the mounting strap about an individual's limb.

A hook and loop fastener patch 28 is mounted onto the exterior surface of the mounting strap 25 cooperative with a fastener web 29 mounted to the mounting strap having a fastener strap hook and loop fastener patch 30. The cradle support 31 is positioned between the fastener web 29 and the hook and loop fastener patch 28 to overlie the first elongate body 11 and maintain its fixed positioning relative to an individual's limb during use of the organization.

The FIGS. 7-11 indicate a modified first body structure having an illumination conduit 33 directed into the first cavity 12 in adjacency to the conical recess 21. Transparent lenses 43 are angularly oriented in adjacency to the conical recess 21, with one of the transparent lenses 34 in communication with the illumination conduit 33, whereupon an illumination flashlight 35 mounted within the illumination conduit 33 directs illumination into one of the transparent lenses 34. Upon the spherical plug 22 being projected against the conical recess 21, illumination into the first cavity 12 as viewed through the remaining transparent lenses 34 is limited due to the orientation of the spherical plug within the conical recess, and accordingly visual indication of reverse flow within the first cavity is afforded to an observer indicating improper flow relative to a patient receiving intravenous fluid.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A valved intravenous needle assembly, comprising,
   a first elongate body having a first cylindrical cavity of a first diameter defined about a predetermined axis, wherein the first body includes a first body end wall, with a second elongate body mounted to the first body coaxially aligned relative to the axis in a spaced relationship relative to the first body end wall, the first body end wall including a tubular needle projecting therefrom in fluid communication with the first cylindrical cavity, and
   the second body having a second cavity, and a web mounted to the first body and to the second body at an interface of the first cavity to the second cavity, with a web bore directed through the web to effect fluid communication between the first cavity and the second cavity, and the second cavity including a delivery tube arranged for reception within the second cavity, and an apertured barrier plate mounted within the first cavity spaced from the first end wall, and a conical recess formed at a further end of the first cavity spaced from the barrier plate and the first body end wall, wherein the conical recess is coaxially aligned with the first cavity and the second cavity, and medially intersected by the web bore, and a floating spherical plug having a second diameter less than the first diameter positioned within the first cavity between the barrier plate and the conical recess and arranged for reception within the conical recess to prevent fluid flow through the web bore, and an abutment ring mounted about the first body spaced from the first body end wall a predetermined length, and a mounting strap, the mounting strap including a cradle support, the cradle support including a semi-cylindrical cavity, with the semi-cylindrical cavity having a length equal to the predetermined length to complementarily receive the first body between the abutment ring and the first body end wall.

2. An assembly as set forth in claim 1 wherein the mounting strap includes a hook and loop fastener patch on an exterior surface of the mounting strap adjacent a first side of the cradle support, and a fastener web mounted to the mounting strap, with the cradle support oriented between the fastener web and the hook and loop fastener patch, and the fastener web including a fastener web hook and loop fastener patch for securement to the hook and loop fastener patch.

3. An assembly as set forth in claim 2 including a plurality of transparent lenses positioned into the first body in adjacency to the conical recess. with an illumination conduit mounted to the first body in surrounding relationship to one of the transparent lenses, and an illumination flashlight directed into the illumination conduit to direct illumination into said one of said lenses.

* * * * *